(12) United States Patent
Stringham et al.

(10) Patent No.: US 12,029,469 B2
(45) Date of Patent: Jul. 9, 2024

(54) SURGICAL SHEARS HAVING FERROMAGNETIC HEATER

(71) Applicant: Domain Surgical, Inc., Salt Lake City, UT (US)

(72) Inventors: Mark Stringham, Kearns, UT (US); Preston Manwaring, Farmington, UT (US); Philip Eggers, Cottonwood Heights, UT (US); Scott Denis, Murrieta, CA (US)

(73) Assignee: Domain Surgical, Inc., Salt Lake City, UT (US)

( * ) Notice: Subject to any disclaimer, the term of this patent is extended or adjusted under 35 U.S.C. 154(b) by 203 days.

(21) Appl. No.: 16/664,458

(22) Filed: Oct. 25, 2019

(65) Prior Publication Data

US 2020/0129222 A1    Apr. 30, 2020

Related U.S. Application Data

(60) Provisional application No. 62/750,747, filed on Oct. 25, 2018.

(51) Int. Cl.
| | | |
|---|---|---|
| *A61B 18/08* | (2006.01) | |
| *A61B 18/00* | (2006.01) | |
| *H05B 1/02* | (2006.01) | |

(52) U.S. Cl.
CPC .......... *A61B 18/085* (2013.01); *H05B 1/025* (2013.01); *A61B 2018/00077* (2013.01);
(Continued)

(58) Field of Classification Search
CPC ............ A61B 18/1442; A61B 18/1445; A61B 18/1447; A61B 2018/1442; A61B 2018/145; A61B 2018/1452; A61B 2018/1455; A61B 2018/1457; A61B 2018/146; A61B 2018/1462; A61B 17/295; A61B 17/068; G02B 3/14; B60N 2/002; C23C 20/005
See application file for complete search history.

(56) References Cited

U.S. PATENT DOCUMENTS

2013/0134745 A1*  5/2013  Aoki ...................... B60N 2/002
                                                          297/180.12
2014/0012297 A1*  1/2014  Ross .................... A61B 17/295
                                                          606/169
(Continued)

*Primary Examiner* — Joanne M Rodden
*Assistant Examiner* — Nora W Rhodes
(74) *Attorney, Agent, or Firm* — Cozen O'Connor

(57) ABSTRACT

In various embodiments, surgical devices and methods are provided. One such surgical device includes a ferromagnetic heater assembly. The ferromagnetic heater assembly includes an electrical conductor, a ferromagnetic heater, and an encapsulant. The electrical conductor has a first leg, a second leg, and a bend between the first and second legs. The bend is located at a distal tip of the electrical conductor, and the first and second legs are spaced apart from one another between the distal end and a proximal end of the electrical conductor. The ferromagnetic heater is disposed on the first leg of the electrical conductor. The encapsulant at least partially surrounds the ferromagnetic heater and a portion of the second leg opposite the ferromagnetic heater, and a surface of the ferromagnetic heater is at least partially exposed by the encapsulant.

19 Claims, 7 Drawing Sheets

(52) U.S. Cl.
CPC ............ *A61B 2018/00101* (2013.01); *A61B 2018/0013* (2013.01); *A61B 2018/00136* (2013.01); *A61B 2018/00148* (2013.01); *A61B 2018/0063* (2013.01); *A61B 2018/00821* (2013.01)

(56) References Cited

U.S. PATENT DOCUMENTS

| | | | |
|---|---|---|---|
| 2015/0327907 A1* | 11/2015 | Stringham | C23C 30/005 606/29 |
| 2017/0215937 A1* | 8/2017 | Kudo | A61B 18/085 |
| 2017/0215941 A1* | 8/2017 | Kazuno | A61B 18/085 |
| 2017/0296189 A1* | 10/2017 | Vendely | A61B 17/07207 |
| 2021/0055544 A1* | 2/2021 | Yamada | G02B 3/14 |

\* cited by examiner

SURGICAL SHEARS HAVING FERROMAGNETIC HEATER

TECHNICAL FIELD

The present disclosure generally relates to surgical shears devices and methods, and more particularly relates to such devices and methods having a ferromagnetic heater assembly in a first jaw and a heat spreader assembly in a second jaw.

BACKGROUND

Brief Summary

The present disclosure, in part, addresses a desire for surgical tools having opposing jaws which are capable of cutting and sealing tissue, and which maintain a desired alignment between a heater assembly and a heat spreader assembly in the jaws, as well as a desired alignment between the jaws with respect to tissue positioned therebetween. In various embodiments, the present disclosure provides devices and methods capable of cutting and sealing tissue, while maintaining an alignment between a heater assembly and a heat spreader assembly in the jaws, and maintaining an alignment between the jaws with respect to tissue positioned between the jaws. Moreover, the present disclosure provides, in various embodiments, an over-molded heater assembly and an over-molded heat spreader assembly which are over-molded with an encapsulant and which are sized and shaped to snuggly fit within corresponding cavities formed in the jaws. In some embodiments, the encapsulant imparts some flexibility to the heater assembly and heat spreader assembly, which facilitates proper alignment of the heater assembly and heat spreader assembly with respect to tissue positioned between them.

The over-molded heater assembly and heat spreader assembly provide single unified structures which may be properly positioned and bonded into the jaws. The jaws provide the underlying structure to withstand the forces which may be applied in order to compress the tissue between the jaws, while the over-molded assemblies provide the means to conduct heat into the tissue suitable to seal and divide the tissue.

In various embodiments, the over-molded assemblies further function to properly position the tissue facing surfaces of the heater assembly and the heat spreader assembly on the tissue. In various embodiments, the over-molded assemblies provide an appropriate combination of stiffness for proper compression and compliance to allow for alignment compensating for tolerance stack ups and tissue variations. The over-molded encapsulant encapsulates the underlying subassembly structure of the heater assembly and heat spreader assembly, and may electrically and thermally insulate the heater and heat spreader assemblies, as well as seal the assemblies from fluid intrusion.

In various embodiments, the present disclosure provides over-molded construction methods which allow the heater assembly and the heat spreader assembly to be bonded into respective cavities in the jaws, thereby simplifying the jaw assembly methods.

In an embodiment, a surgical device is provided that includes a ferromagnetic heater assembly. The ferromagnetic heater assembly includes an electrical conductor, a ferromagnetic heater, and an encapsulant. The electrical conductor has a first leg, a second leg, and a bend between the first and second legs. The bend is located at a distal tip of the electrical conductor, and the first and second legs are spaced apart from one another between the distal end and a proximal end of the electrical conductor. The ferromagnetic heater is disposed on the first leg of the electrical conductor. The encapsulant at least partially surrounds the ferromagnetic heater and a portion of the second leg opposite the ferromagnetic heater, and a surface of the ferromagnetic heater is at least partially exposed by the encapsulant.

In another embodiment, a surgical device is provided that includes a first jaw having a first cavity, a second jaw having a second cavity, a ferromagnetic heater assembly, and a heat spreader assembly. The second jaw is rotatably coupled to the first jaw about a pivot point. The ferromagnetic heater assembly is positioned in the first cavity of the first jaw and includes an electrical conductor, a ferromagnetic heater, and an encapsulant. The electrical conductor has a first leg, a second leg, and a bend between the first and second legs. The bend is located at a distal tip of the electrical conductor, and the first and second legs are spaced apart from one another between the distal end and a proximal end of the electrical conductor. The ferromagnetic heater is disposed on the first leg of the electrical conductor. The encapsulant at least partially surrounds the ferromagnetic heater and a portion of the second leg opposite the ferromagnetic heater, and a surface of the ferromagnetic heater is at least partially exposed by the encapsulant. The heat spreader assembly is positioned in the second cavity of the second jaw.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with hand held surgical devices and surgical shears have not been shown or described in detail to avoid unnecessarily obscuring descriptions of the embodiments.

Throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

Figure 1:
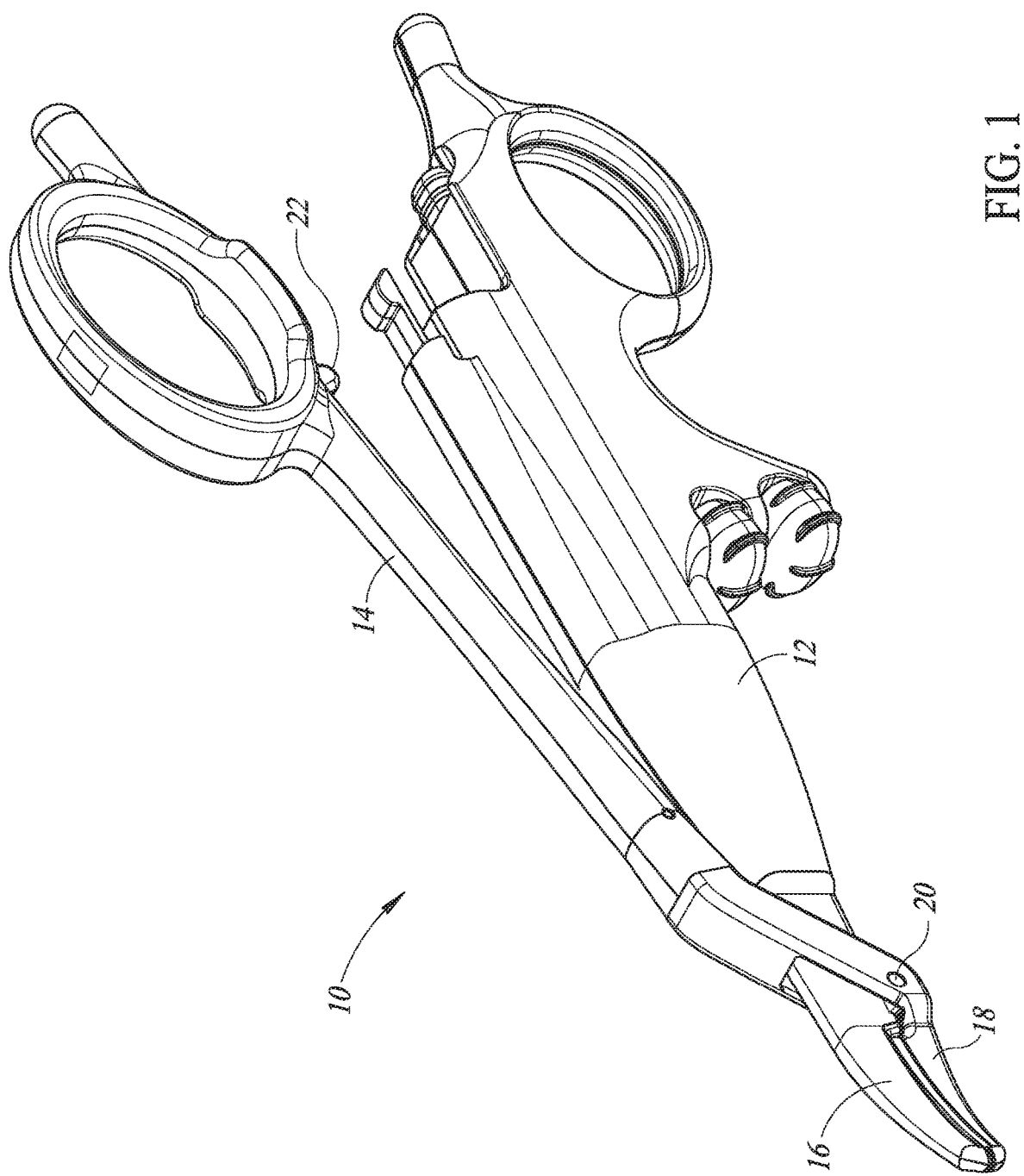
FIG. 1 is a perspective view illustrating a surgical device, in accordance with one or more embodiments.

Turning now to FIG. 1, illustrated therein is a handheld surgical device in the form of open shears 10, in accordance with one or more embodiments of the present disclosure. The open shears 10 includes a body 12 and an arm 14. A first jaw 16 is attached to the body 12, and a second jaw 18 is attached to the arm 14. The first and second jaws 16, 18 are attached to one another by a pivot pin 20, which connects the arm 14 to the body 12.

The second jaw 18 may be moved toward and away from the first jaw 16 by rotation of the arm 14 with respect to the body 12 about the pivot pin 20. The open shears 10 is shown in FIG. 1 in a closed configuration, in which a heater assembly on the first jaw 16 contacts a heat spreader assembly on the second jaw 18. The heater assembly 30 is shown in further detail in FIGS. 3-5, and the heat spreader assembly 50 is shown in further detail in FIGS. 7-9, which will be described in further detail below.

In use, the open shears 10 may be utilized to seal and cut or divide tissue. More particularly, the first and second jaws 16, 18 may be opened, e.g., by rotating the arm 14 away from the body 12, and tissue may be positioned between the open jaws 16, 18 of the open shears 10. The arm 14 may then be rotated toward the body 12, thereby moving the second jaw 18 toward the first jaw 16 into the closed configuration shown in FIG. 1. The tissue may be sealed, cut, and/or divided by heating of the heater assembly 30, which may contact the tissue, and by a compression force applied to the tissue by the jaws 16, 18.

As shown in FIG. 1, a proximal portion of the arm 14 may be spaced apart from the body 12 when the jaws 16, 18 are brought together in the closed configuration (e.g., with the heater assembly 30 in contact with the heat spreader assembly 50). In some embodiments, the arm 14 is formed of a material having sufficient flexibility such that the arm 14 may be flexed toward the body 12, and in some embodiments, the arm 14 may be flexed toward the body 12 to a point at which a protrusion 22 on the arm 14 contacts an opposite surface of the body 12. This flexibility of the arm 14 facilitates application of additional compression force to tissue positioned between the first and second jaws 16, 18, and the compression force may be controlled by the user.

Figure 2:
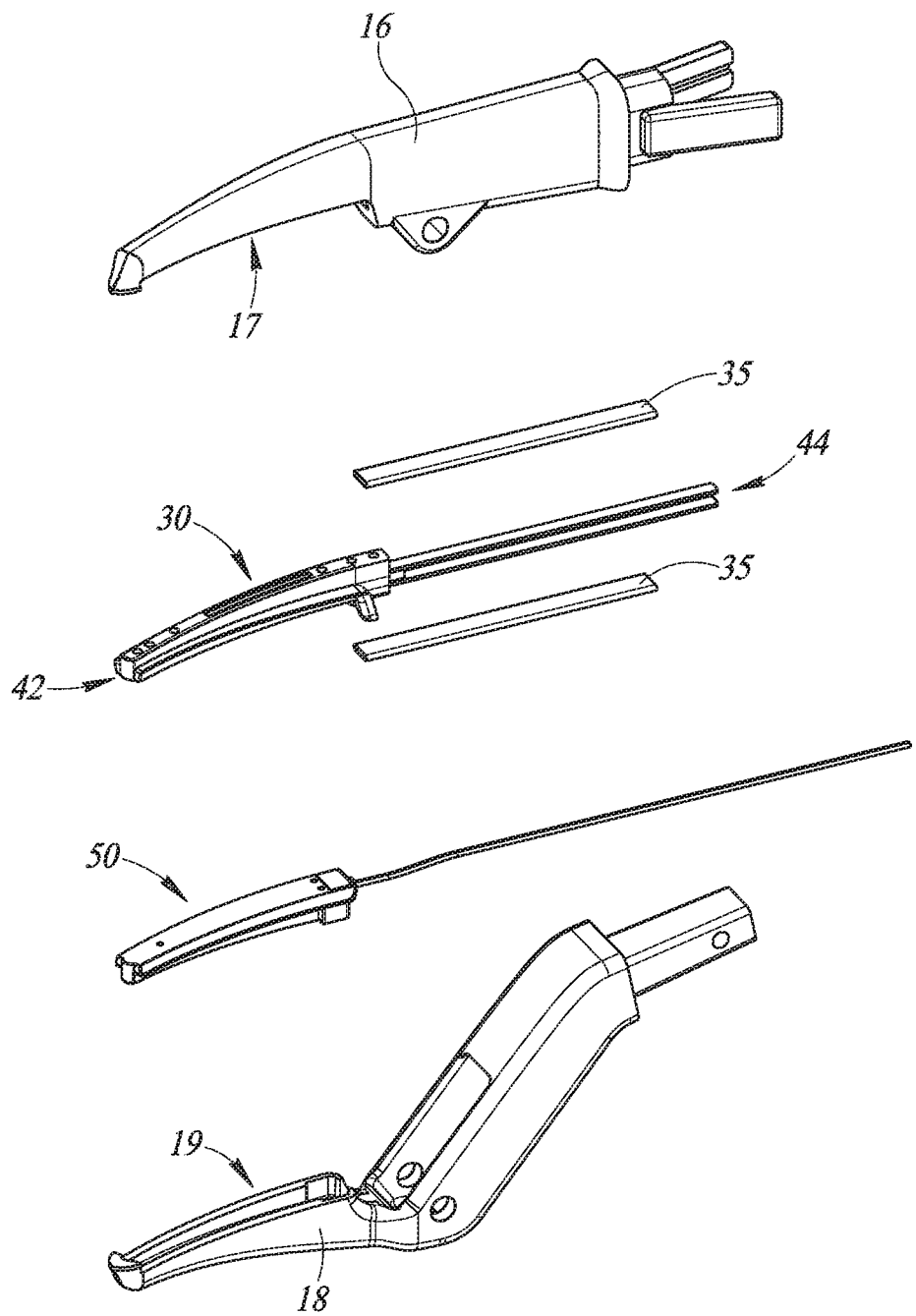
FIG. 2 is a partially exploded view illustrating a heater assembly, a heat spreader assembly, and jaws of the surgical device shown in FIG. 1, in accordance with one or more embodiments.

FIG. 2 is a diagram illustrating further details of the first and second jaws 16, 18, as well as the heater assembly 30 and the heat spreader assembly 50. In some embodiments, each of the first and second jaws 16, 18 includes a metal jaw structure, which may be coated with a nonstick and/or nonreactive material, such as Polytetrafluoroethylene (PTFE). The first jaw 16 may be referred to herein as a "fixed" jaw, as it is connected to the body 12 of the open shears 10, and the second jaw 18 may be referred to herein as a "movable" jaw, as it is movable with respect to the first jaw 16, e.g., by rotation of the arm 14.

As will be discussed in further detail below, the heater assembly 30 may be inserted into a cavity 17 in the first jaw 16, and the heat spreader assembly 50 may be inserted into a cavity 19 in the second jaw 18. The heater assembly 30 and the heat spreader assembly 50 may have shapes and sizes which respectively correspond to the shapes and sizes of the cavities 17, 19 of the first and second jaws 16, 18. Accordingly, the heater assembly 30 may be inserted into the cavity 17 of the first jaw 16, which provides a snug fit between the heater assembly 30 and the first jaw 16 and which prevents or reduces intrusion of moisture, fluids, eschar or the like into the first jaw 16. Similarly, the heat spreader assembly 50 may be inserted into the cavity 19 of the second jaw 18, which provides a snug fit between the heat spreader assembly 50 and the second jaw 18 and which prevents or reduces intrusion of moisture, fluids, eschar or the like into the second jaw 18. In some embodiments, the heater assembly 30 and the heat spreader assembly 50 may be adhered within the respective cavities 17, 19 of the jaws 16, 18 by an adhesive material. In other embodiments, the heater assembly 30 and the heat spreader assembly 50 may be held within the respective cavities 17, 19 of the jaws 16, 18 by mechanical retention. For example, the heater assembly 30 and the heat spreader assembly 50 may be mechanically retained within the respective cavities 17, 19 of the jaws 16, 18 due to the corresponding shapes and sizes of the heater assembly 30 and the cavity 17 of the first jaw 16, and/or the corresponding shapes and sizes of the heat spreader assembly 50 and the cavity 19 of the second jaw 18. In some embodiments, the heater assembly 30 and the heat spreader assembly 50 and the cavities 17, 19 of the jaws 16, 18 may be sized and shaped to provide a snap-fit between the heater assembly 30 and the cavity 17 of the first jaw 16, and between the heat spreader assembly 50 and the cavity 10 of the second jaw 18.

In some embodiments, the first and second jaws 16, 18 may be formed of a metal material having high strength and thermal conductivity properties. In some embodiments, the first and second jaws 16, 18 may be formed of a die cast zinc alloy, such as EZAC.

In some embodiments, the interior surfaces of the cavities 17, 19 of the first and second jaws 16, 18 may be treated, e.g., by application of a chemical primer, bead blasting and/or plasma etching, which may facilitate suitable adhesion between the heater assembly 30 and heat spreader assembly 50 and the first and second jaws 16, 18, respectively. In some embodiments, the heater assembly 30 and heat spreader assembly 50 may be attached within the cavities 17, 19 of the first and second jaws 16, 18, respectively, by an adhesive. In some embodiments, the adhesive comprises a liquid silicone rubber, and in some embodiments, the liquid silicone rubber has a durometer of about 40, although embodiments of the present disclosure are not limited thereto.

In various embodiments, the heater assembly 30, heat spreader assembly 50, and the cavities 17, 19 of the jaws 16, 18 may have various different shapes and sizes, depending, for example, on application. For example, different surgical tools may have different sizes and shapes of the jaws, depending on the intended anatomical use of such tools.

Figure 3:
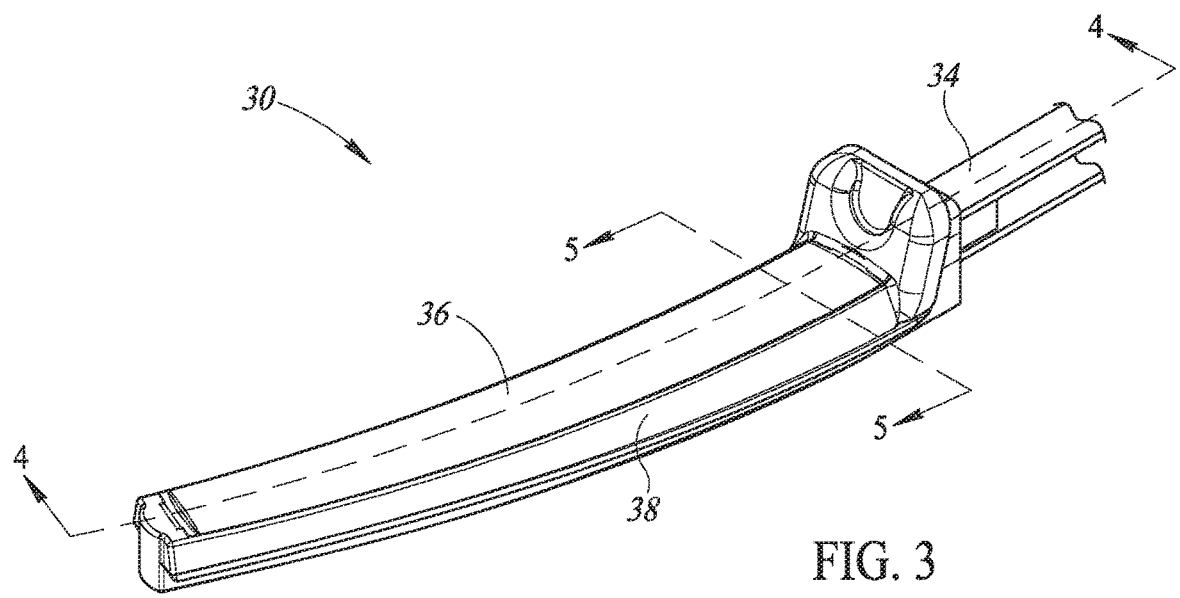
FIG. 3 is a perspective view of the heater assembly of the surgical device shown in FIG. 2, in accordance with one or more embodiments.
Figure 4:
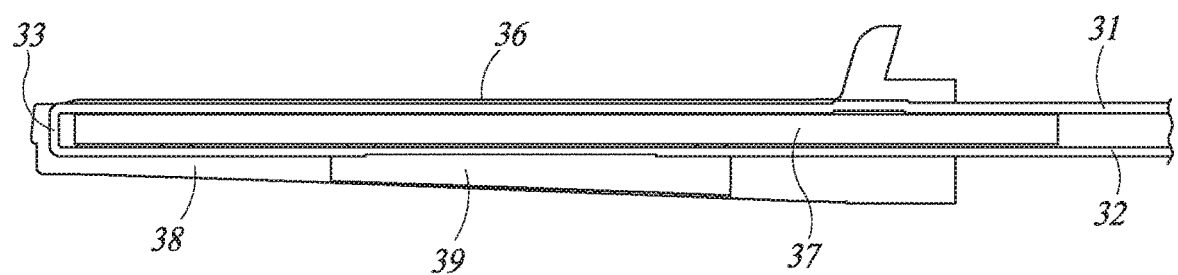
FIG. 4 is a cross-sectional view taken along the cut line 4-4 of FIG. 3, illustrating further details of the heater assembly, in accordance with one or more embodiments.
Figure 5:
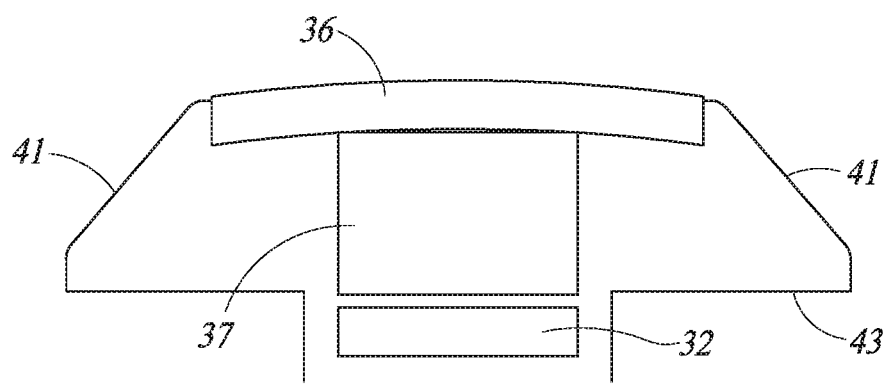
FIG. 5 is a cross-sectional view taken along the cut line 5-5 of FIG. 3, illustrating further details of the heater assembly, in accordance with one or more embodiments.

As shown in FIGS. 3-5, the heater assembly 30 includes an electrical conductor 34, a ferromagnetic heater 36, and an encapsulant 38. The electrical conductor 34 includes a first leg 31, a second leg 32, and a bend 33 between the first and second legs 31, 32. In some embodiments, the electrical conductor 34 may be a single strip or length of electrically conductive material, which is bent, e.g., at the bend 33, between the first and second legs 31, 32. The bend 33 may be located at a distal tip of the electrical conductor 34, and the first and second legs 31, 32 may be spaced apart from one another between the distal end 42 and a proximal end 44 of the electrical conductor 34.

The ferromagnetic heater 36 may be disposed on the first leg 31 of the electrical conductor 34. In some embodiments, the ferromagnetic heater 36 includes a coating of ferromagnetic material on the first leg 31 of the electrical conductor 34.

The encapsulant 38 at least partially surrounds the ferromagnetic heater 36 and a portion of the second leg 32 opposite the ferromagnetic heater 36. For example, as shown in FIG. 3, the encapsulant 38 surrounds the portion of the second leg 32 that is below the ferromagnetic heater 36, and further surrounds sides of the electrical conductor 34, including sides of the first leg 31, the second leg 32, and the bend 33. A surface of the ferromagnetic heater 36 is at least partially exposed by the encapsulant 38. For example, as shown in FIG. 3, an upper surface of the ferromagnetic heater 36 is at least partially exposed by the encapsulant 38. The exposed surface of the ferromagnetic heater 36 may be a tissue-contacting surface, which may contact tissue during use of the open shears 10. In some embodiments, an entire surface of the ferromagnetic heater 36 is exposed, which may form the tissue-contacting surface of the ferromagnetic heater 36.

In some embodiments, the encapsulant 38 may be formed of a thermally insulating material having a low thermal conductivity and a low heat capacity. The thermal insulating characteristics of the encapsulant 38 reduce thermal conduction, for example, between the ferromagnetic heater 36 and the surrounding features of the open shears 10, such as the second leg 32 of the conductor 32, as well as the surfaces of the first jaw 16.

In some embodiments, the encapsulant 38 may be formed of an electrically insulating material, which may electrically isolate the electrical conductor 34 within the encapsulant 38, and which may prevent electrical shorts between the conductor 34 and the first jaw 16.

In some embodiments, the encapsulant 38 may be formed of a non-stick material, which may prevent or reduce the occurrence of tissue sticking to the heater assembly 30 during use. To achieve good sealing of tissue, it is important to avoid sticking of the tissue to the heater assembly 30. Any such sticking of tissue may tend to rip open the seals that are formed in the tissue upon opening of the jaws 16, 18. Accordingly, by forming the encapsulant 38 of a non-stick material, tissue sealing may be improved. Moreover, the encapsulant 38 may be formed of a material suitable for sealing the encapsulated components (such as the electrical conductor 34, the ferromagnetic heater 36, and the like) and to prevent the permeation of moisture, fluids, eschar or the like.

In some embodiments, the encapsulant 38 may be formed of a silicone-containing material, such as silicone rubber. Silicone rubber has a low thermal conductivity and a low heat capacity. Moreover, silicone rubber has a high dielectric constant and acts as a good electrical insulator since it encapsulates the portions of the electrical conductor 32 and the ferromagnetic heater 36 which form the heating element of the heater assembly 30. Additionally, silicone rubber is a suitable encapsulant material which may form sealed outer surfaces of the heater assembly 30, thereby avoiding the presence of nooks and crannies where fluids and eschar could otherwise accumulate. The surface characteristics of silicone make the silicone rubber a suitably non-stick material for use in the open shears 10.

In some embodiments, the heater assembly 30 includes a thermally insulating spacer 37 positioned between the first and second legs 31, 32 of the electrical conductor 34. As shown in FIG. 4, the electrical conductor 34 may be bent approximately 180° (e.g., at the bend 33) so that the return leg (e.g., the second leg 32) of the electrical conductor 34 is positioned below the tissue facing portion of the first leg 31 of the conductor 34 where the ferromagnetic heater 36 is disposed, and the spacer 37 is between the first and second legs 31, 32 of the conductor 34. In some embodiments, the spacer 37 may be a laser etched spacer formed of a polyimide, such as Kapton.

The spacer 37 provides several advantageous features and functionalities to the heater assembly 30. For example, the spacer 37 provides stiffness to the heater assembly 30. More particularly, the spacer 37 provides a solid structure between the first and second legs 31, 32 of the electrical conductor 34, which imparts stiffness to the comparatively flexible first and second legs 31, 32 of the electrical conductor 34.

In some embodiments, insulators 35 (FIG. 2) may be positioned over one or both of the first and second legs 31, 32 of the conductor. The insulators 35 may be formed of any electrically insulating material, and in some embodiments, the insulators 35 are formed of an electrically and thermally insulating material. In at least one embodiment, the insulators 35 are formed of a polyimide, such as Kapton, and have a tubular shape which permits sliding the insulators 35 over the first and second legs 31, 32 of the conductor 34.

Additionally, the spacer 37 at least partially defines the geometry of the first and second legs 31, 32 of the conductor 34, for example, by maintaining a desired spacing between the first and second legs 31, 32. By maintaining the spacing between the first and second legs 31, 32 at a particular distance, the electrical impedance of the heating element (i.e., the electrical conductor 34 and the ferromagnetic heater 36) may be maintained at a desired value. For example, in some embodiments, the heating element (i.e., the electrical conductor 34 and the ferromagnetic heater 36) may be designed to have a particular impedance value, and in some embodiments, the heating element forms a part of a tuned electrical circuit in which the impedance of the heating element is tuned to match a source impedance of a power supply (not shown) and a cable, such as a coaxial cable, that electrically couples the power supply to the heating element. The spacer 37 thus reduces or prevents variations in the spacing between the first and second legs 31, 32 of the conductor 34, thereby maintaining a substantially same or constant impedance value of the conductor 34 and the ferromagnetic heater 36. In contrast, if the legs 31, 32 of the conductor 34 were to flex significantly (e.g., in the absence of the spacer 37), for example, during tissue compression or activation, the spacing between the legs 31, 32 may vary which may cause detuning of the impedance matched circuit, which would result in losses in the energy transfer between the source (e.g., the power supply) and the load (e.g., the electrical conductor 34 and the ferromagnetic heater 36).

Moreover, the spacer 37 may be made of a thermally insulating material. That is, the spacer 37 may have a low thermal conductivity. In some embodiments, the spacer 37 is formed of a polyimide, such as Kapton, which can tolerate very high temperatures and has a low thermal conductivity. The spacer 37 thus acts as an insulator between the ferromagnetic heater 36 on the first leg 31 of the conductor 34 and the comparatively cooler second leg 32 of the conductor 34.

In some embodiments, the heater assembly 30 includes a second spacer 39, which may be located opposite the spacer 37, with the second leg 32 of the conductor 34 between the spacer 37 and the second spacer 39. As shown in FIG. 4, the second spacer 39 may have a tapered shape that extends along a portion of the length of the ferromagnetic heater 36. In some embodiments, the second spacer 39 may be molded from a high temperature material, such as a molded polyetherimide material like Ultem. In other embodiments, the second spacer 39 may be etched or cut from a Kapton material.

The second spacer 39 provides vertical stiffening in a central region of the heater assembly 30, which when assembled into the cavity 17 of the first jaw 16, provides vertical stiffening to a region where tissue is most commonly positioned and compressed. This ensures that the tissue is subjected to the full force of compression when the arm 14 of the open shears 10 is fully closed.

In some embodiments, the second spacer 39 has a length that is less than a length of the encapsulant 38. In such embodiments, the distal and proximal ends of the heater assembly 30, when inserted into the cavity 17 of the first jaw 16, are primarily supported by the encapsulant 38, which is positioned between a surface of the cavity 17 of the first jaw 16 and the distal and proximal ends of the heater assembly 30. The encapsulant 38, which may be, for example, silicone rubber, may be compliant or flexible. Hence, the encapsulant 38 may have a tendency to flex under pressure. This allows the exposed surface of the ferromagnetic heater 36 to tilt slightly when the tissue thickness is irregular along the length of the first jaw 16 or if there are minor tolerance stack ups in the assembly of the jaws 16, 18 (including the heater assembly 30 and the heat spreader assembly 50) which affect the alignment of the heater assembly 30 and the heat spreader assembly 50.

In some embodiments, the second spacer 39 has a length that is less than a length of the spacer 37, as shown in FIG. 4.

In other embodiments, the second spacer 39 may be omitted, and the encapsulant 38 may be formed to have a same or similar shape as shown in FIG. 4, with the encapsulant 38 filling the area beneath the lower surface of the second leg 32 of the conductor 34. For example, the encapsulant 38 may be formed of a semi-flexible material which provides suitable stiffness to properly align and maintain the desired positioning of the heater assembly 30 within the cavity 17 of the first jaw 16. In still other embodiments, the encapsulant 38 is a silicone rubber having a stiffness of about 80 durometer, which provides suitable stiffness to the heater assembly 30 without the presence of the second spacer 39.

In some embodiments, the first jaw 16 may include a stiffener structure, e.g., within the cavity 17, that functions similarly to the second spacer 39, for example, by providing additional stiffness to the heater assembly 30 when inserted into the cavity 17 of the first jaw 16.

The heater assembly 30 may be an over-molded assembly sized to fit snuggly within the cavity 17 of the first jaw 16. For example, the entire structure of the heater assembly 30 that fits within the cavity 17 of the first jaw 16 may be over-molded with the encapsulant 38, which may be a silicone rubber having a durometer hardness value between about 40 and 100. In some embodiments, the encapsulant 38 is a liquid silicone rubber (LSR) having a durometer hardness value of about 80. However, embodiments of the present disclosure are not limited thereto, and the encapsulant 38 may include other materials having different durometer values.

In some embodiments, the underlying structure of the heater assembly 30, e.g., the electrical conductor 34, the ferromagnetic heater 36, the spacer 37 and/or the second spacer 39, may be pre-assembled and treated for improved adhesion by the encapsulant 38 (e.g., liquid silicone rubber) using plasma etching and solvent treatment. The structure may then be placed in a mold and the encapsulant material (e.g., LSR) may be injected into the mold. The encapsulant 38 may be formed to cover the sides, bottom and interior of the heater assembly 30; however, the active portion of the ferromagnetic heater 36 (e.g., the upper surface of the ferromagnetic heater, as shown in FIG. 3) remains exposed. This exposed surface of the ferromagnetic heater 36 forms the surface which, in use, contacts the compressed tissue and conducts heat into it.

The first and second legs 31, 32 of the conductor 34 extend back (e.g., proximally) from the over-molded portion of the structure. Otherwise stated, the over-molded portion of the structure, i.e., the portion where the encapsulant 38 is provided, does not entirely cover the first and second legs 31, 32 of the conductor 34. Instead, portions of the first and second legs 31, 32 extend proximally from the encapsulated heater assembly 30. When assembled into the cavity 17 of the first jaw 16, the first and second legs 31, 32 may extend distally through a hole in the center of the first jaw 16, and the first and second legs 31, 32 may be soldered directly to corresponding circuitry within the body 12 of the open shears. For example, the first and second legs 31, 32 may be electrically coupled, by soldering, to power supply or other circuitry on a printed circuit board (PCB) in the body 12.

As shown in FIG. 5, side surfaces 41 of the encapsulant 38 are beveled away from the ferromagnetic heater 36 at a fairly steep angle. The beveled side surfaces 41 of the encapsulant 38 provides a surface transition from between the ferromagnetic heater 36 and outer surfaces of the first jaw 16 which facilitates proper sealing and dividing of tissue during use. If the surface of the encapsulant 38 extended outward at a same height or level as the adjacent surface of the ferromagnetic heater 36, or if the surface of the encapsulant 38 is beveled at too shallow of an angle, then the surfaces of the encapsulant 38 could undesirably entrap unsealed tissue and prevent it from falling away when the seal and divide cycle is completed. Conversely, if the surface of the encapsulant 38 is beveled at too steep of an angle, it could undesirably diminish the amount of material on a lower surface 43 of the encapsulant 38 available for bonding to the corresponding surfaces of the cavity 17 in the first jaw 16. In some embodiments, the side surfaces 41 may have a bevel angle (e.g., with respect to an upper surface of the adjacent ferromagnetic heater 36) that is within a range of 30° to 60°, inclusive.

Since the beveled surfaces 41 of the encapsulant 38 may contact tissue, in some embodiments, the encapsulant 38 is formed of a biocompatible material, such as silicone rubber as described elsewhere herein. Silicone rubber is a very biocompatible material. Moreover, as previously discussed, silicon rubber is a comparatively non-stick material, which prevents build up of tissue and eschar on its surface.

Figure 6:
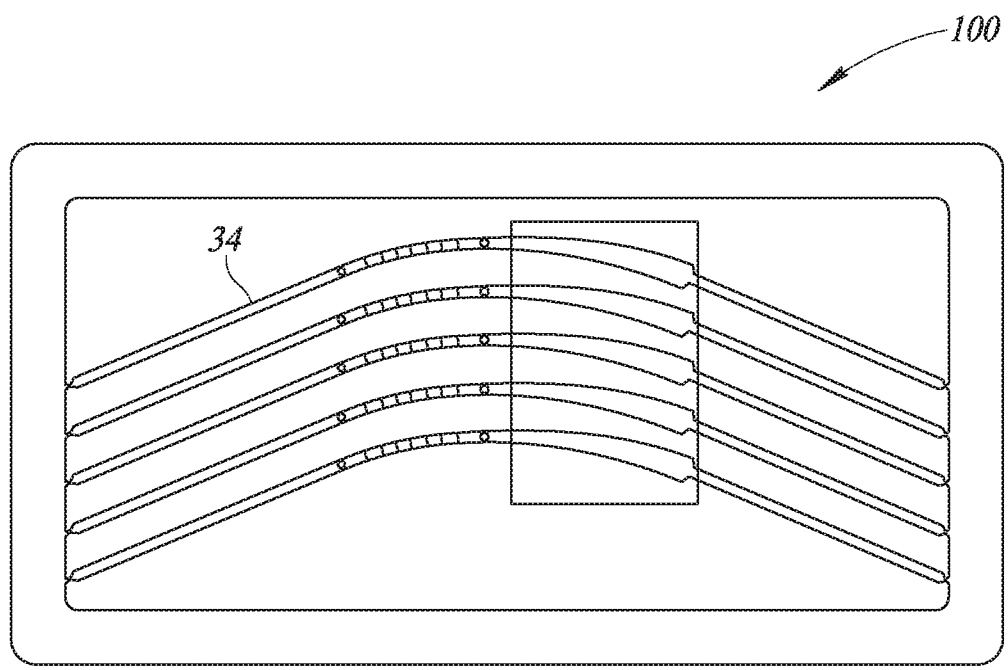
FIG. 6 is a top view illustrating a multi-unit frame including a plurality of conductors, in accordance with one or more embodiments.

FIG. 6 is a top view illustrating a multi-unit frame 100 including a plurality of conductors 34. The conductors 34 may be formed to have a desired shape, for example, by etching the multi-unit frame 100, which may be a sheet of conductive material. In some embodiments, the multi-unit frame 100 is a sheet of beryllium copper (BeCu) having a thickness between about 0.005 inch and 0.02 inch, inclusive. In some embodiments, the multi-unit frame 100 is a sheet of beryllium copper having a thickness of about 0.012 inch. The conductors 34 formed in the multi-unit frame 100 may have a same thickness as the multi-unit frame 100. The conductors 34 may be formed of a material (e.g., the material of the multi-unit frame 100) which has sufficient malleability to bend the conductors 34 180°, yet which also has a hardness sufficient to withstand the compression forces, for example, during use of the open shears 10.

In various embodiments, different techniques may be utilized to form the conductors 34, including, for example, by stamping the conductors 32 from a sheet of conductive material.

The conductors 34 may be formed of any electrically conductive material. In some embodiments, the conductors 34 are formed of BeCu, which has high electrical and thermal conductivity, and further has a suitable malleability (e.g., for forming the bend 33 in the conductor 34) and stiffness (e.g., for application of suitable compression forces to tissue).

The tissue facing profile of the heating element (e.g., the exposed surface of the ferromagnetic heater 36) may be formed or stamped in the panel 100. In some embodiments, the exposed surface of the ferromagnetic heater 36 which contacts tissue may have a convex shape, as shown, for example, in FIG. 5. The convex surface of the ferromagnetic heater 36 may have a slight rise along a center line of the surface, as shown. In some embodiments, the rise along the center line of the ferromagnetic heater 36 may be within a range of about 0.001 inch to about 0.01 inch, inclusive, with respect to the lateral edges of the exposed surface of the ferromagnetic heater 36. In one or more embodiments, the rise along the center line of the ferromagnetic heater 36 may be about 0.004 inch. The center line of the convex shape of the exposed surface of the ferromagnetic heater 36 provides a line or surface at which opposing surfaces of the ferromagnetic heater 36 and the heat spreader assembly 50 contact one another to cut tissue, e.g., when the first and second jaws 16, 18 are closed. The relatively lower sides of the ferromagnetic heater 36 facilitate sealing of the tissue. In various embodiments, the exposed surface of the ferromagnetic heater 36 may have other shapes which may concentrate heating energy along a desired tissue cutting line.

To create the desired heating effect in the desired area the length of the tissue facing area of the ferromagnetic heater 36 may be formed by plating a portion of the conductor 34 with a ferromagnetic material. In some embodiments, the ferromagnetic material is a nickel-iron alloy, such as Niron. In one or more embodiments, the plated ferromagnetic material has a thickness in a range of about 4 to 5 skin depths, inclusive. In another aspect, the plated ferromagnetic material is sufficiently thin to avoid damage to the ferromagnetic heater 36 due to the high thermally induced stresses during heating and cooling.

The underlying heating mechanism is due to the current flowing in the ferromagnetic plating of the ferromagnetic heater 36 being forced to crowd into a narrow cross-sectional area. At high frequencies, the current flowing in a conductor is crowded into its outer skin. This current concentration is affected by the conductivity and magnetic permeability of the material it is flowing through. The skin effect is due to eddy currents. Eddy current losses and the skin effect current crowding are synonymous in this context as they explain the resistive heating losses. The skin depth of a conductive wire is expressed by the following equations:

$$\delta = \sqrt{2\rho/\omega\mu} = 1/\sqrt{\pi f \mu \sigma}$$

Where:
$\delta$=skin depth (or penetration depth)
$\rho$=resistivity of the conductor
$\omega$=angular frequency of current=$2\pi f$
$\mu$=absolute magnetic permeability of conductor
$\sigma$=conductivity of the conductor The current density in the wire is expressed by the following equation.

$$J = J_s e^{-d/\delta}$$

Where:
$J_S$=the current at the surface of the conductor.

Virtually all of the current in the conductor is within the first 5 skin depths. The skin depth is a function of the frequency of the applied current in the conductor and the magnetic permeability of the ferromagnetic material. At 40.68 MHz this translates to a thickness of about 5-50 μm depending on the permeability of the ferromagnetic material. In some embodiments, the ferromagnetic plating of the ferromagnetic heater has a thickness within a range of about 5 μm to about 50 inclusive. In one or more embodiments, the ferromagnetic plating of the ferromagnetic heater has a thickness of about 10 μm.

After forming the ferromagnetic heater 36, e.g., by plating the conductor 34 with a ferromagnetic material, the ferromagnetic heater 36 may be coated with a non-stick material. In some embodiments, the ferromagnetic heater 36 is coated with a chromium nitride (CrN) material, which prevents oxidation and provides a non-stick layer on the tissue facing surface of the ferromagnetic heater 36. Moreover, the CrN coating may serve to put the ferromagnetic plating (e.g., Niron) in compression.

Figure 7:
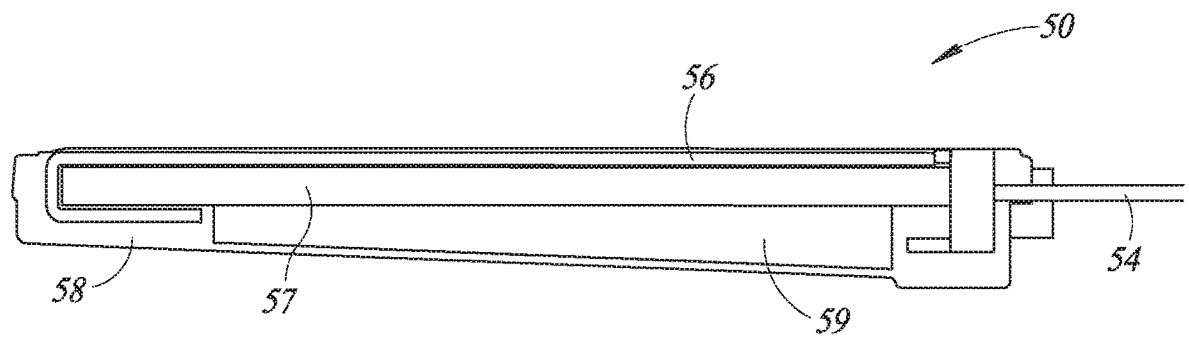
FIG. 7 is a lengthwise cross-sectional view of the heat spreader assembly of the surgical device shown in FIG. 2, in accordance with one or more embodiments.
Figure 8:
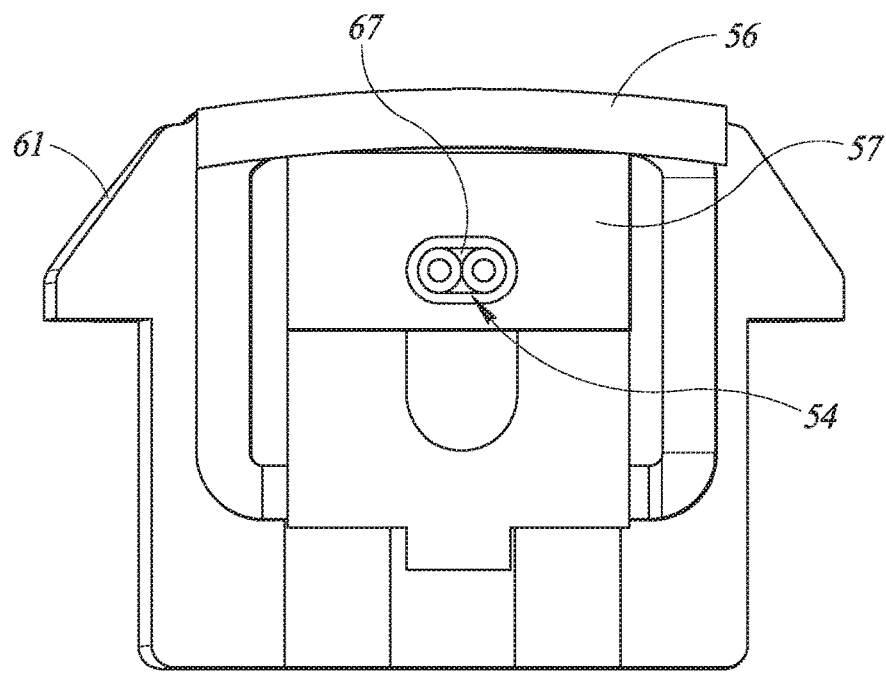
FIG. 8 is a widthwise cross-sectional view of the heat spreader assembly of the surgical device shown in FIG. 2, in accordance with one or more embodiments.
Figure 9:
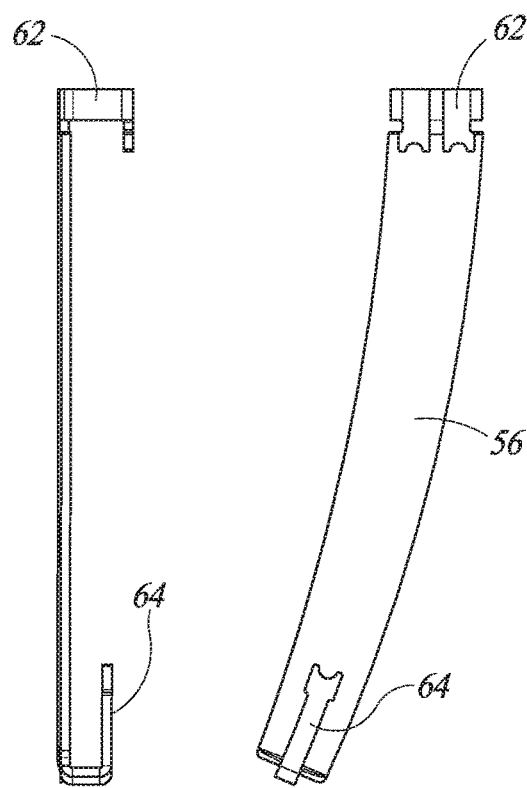
FIG. 9 is a diagram illustrating further details of the heat spreader of the heat spreader assembly, in accordance with one or more embodiments.

FIGS. 7-9 illustrate further details of the heat spreader assembly 50. The construction of the second jaw 18, including the heat spreader assembly 50, may be substantially similar, in many respects, to the construction of the first jaw 16 including the heater assembly 30, except that the second jaw 16 and heat spreader assembly 50 function as a heat spreader (e.g., to uniformly spread received heat) and to monitor the temperature of the tissue.

During sealing and dividing the tissue is compressed between the first and second jaws 16, 18 and heat is conducted across the tissue from the ferromagnetic heater 36 to the heat spreader 56 of the heat spreader assembly 50. Heat is only conducted where there is tissue lying between the ferromagnetic heater 36 and the heat spreader 56. In addition, the thermal conductivity of the tissue may vary within that area. In some embodiments, the heat spreader 56 is formed of a material having a high thermal conductivity, which evens out or spreads the temperature along the length of the heat spreader 56 thereby making the temperature of the tissue more uniform, which facilitates uniform dividing and sealing of the tissue.

In some embodiments, the heat spreader assembly 50 includes a heat spreader 56, a first spacer 57, a second spacer 59, a temperature sensor 54 coupled to the heat spreader 56, and an encapsulant 58 which at least partially encapsulates the interior features of the heat spreader assembly 50 and which has a shape and size to snuggly fit within the cavity 19 of the second jaw 18.

The heat spreader 56 is similar, in some respects, to the conductor 34 of the heater assembly 30, except that the heat spreader 56 does not include first and second legs for receiving electrical current. In some embodiments, the heat spreader 56 may include a same material as the conductor 34. In some embodiments, the heat spreader 56 may include a substrate of a thermally conductive material, such as beryllium copper (BeCu). In some embodiments, the heat spreader 56 may be coated with a ceramic layer, such as a layer of chromium nitride (CrN), which may prevent oxidation and may further provide a non-stick layer on the surface of the heat spreader 56.

The encapsulant 58 at least partially surrounds or encapsulates the heat spreader 56. A surface of the heat spreader 56 is at least partially exposed by the encapsulant 58. For example, as shown in FIG. 7, an upper surface of the heat spreader 56 is at least partially exposed by the encapsulant 58. The exposed surface of the heat spreader 56 may be a tissue-contacting surface, which may contact tissue during use of the open shears 10. In some embodiments, the exposed surface of the heat spreader 56 may be aligned opposite to, and may have a substantially same or corresponding shape as, the exposed surface of the ferromagnetic heater 36. In use, the exposed surfaces of the heat spreader 56 and the ferromagnetic heater 36 may be brought together into contact with one another, or into contact with tissue positioned therebetween.

The temperature sensor 54 is thermally coupled to the heat spreader 56 and may be used to monitor the temperature of the heat spreader 56. In some embodiments, the temperature sensor 54 is physically and thermally coupled to the heat spreader 56, and the temperature sensor 54 directly senses a temperature of the heat spreader 56. The temperature sensor 54 may be any sensor capable of sensing heat, such as a temperature of the heat spreader 56. In one or more embodiments, the temperature sensor 54 may be a thermocouple, such as a type J thermocouple which has iron and constantan wires. The temperature sensor 54, such as a thermocouple, may be physically coupled to a back (or proximal) side of the heat spreader 56, for example, by welding.

Since the heat spreader 56 does not have return legs, tabs 62 which extend laterally from a proximal end of the heat spreader 56 may be folded or bent at least partially around the first spacer 57 to retain the first spacer 57 in a desired position with respect to the heat spreader 56 within the encapsulant 58. A distal tab 64 may extend from a distal tip of the heat spreader 56, and may be folded around a distal end of the first spacer 57. The tabs 62, 64 may be bent 180° around respective portions of the first spacer 57, which may hold the heat spreader 56 on the first spacer 57 and may fix relative positions of the heat spreader 56 and the first spacer 57 within the encapsulant 58.

The first spacer 57 may be substantially similar to the spacer 37 in the heater assembly 30, described above. In some embodiments, the first spacer 57 may be a laser etched spacer formed of a polyimide, such as Kapton. The first spacer 57 may be positioned under the heat receiving surface (e.g., the upper surface) of the heat spreader 56 and serves the same functions as described above with respect to the spacer 37 of the heater assembly 30. For example, the first spacer 57 of the heat spreader assembly 50 may serve as a lateral stiffener and a thermal and electrical insulator. In some embodiments, the first spacer 57 may be laser etched out of Kapton sheet having a thickness of about 0.040 inches, and in some embodiments, the first spacer 57 may include a hole 67 through which wires of the temperature sensor 54 (e.g., thermocouple wires) may exit.

In one or more embodiments, the heat spreader assembly 50 includes a second spacer 59, which may have a tapered surface (e.g., lower surface) and which may be substantially similar to, and may include any of the same features and functionalities as described above with respect to, the second spacer 39 of the heater assembly 30. The second spacer 59 of the heat spreader assembly 50 may extend along a portion of the length of the heat spreader assembly 50 and adds vertical stiffness. In some embodiments, the second spacer 59 directly contacts the first spacer 57.

A channel (e.g., extending along a length direction) may be formed in one or both of the first spacer 57 and the second spacer 59, which may provide a path for wires of the temperature sensor 54 (e.g., thermocouple wires) to be routed to the rear (e.g., proximal end) of the heat spreader assembly 50. In some embodiments, the second spacer 59 is molded out of a high temperature material, such as Ultem.

In other embodiments, the first spacer 57 and/or the second spacer 59 of the heat spreader assembly 50 may be omitted, and the encapsulant 58 may be formed to fill the area beneath the lower surface of the heat spreader 56.

The encapsulant 58 of the heat spreader assembly 50 may be substantially the same as the encapsulant 38 of the heater assembly 30, described above. For example, the encapsulant 58 may be formed of a silicon rubber which may be over-molded to form outer surfaces of the heat spreader assembly 50 on the sides and on the bottom, and which may have a size and shape which provides a snug fit within the cavity 19 of the second jaw 18.

In some embodiments, the encapsulant 58 of the heat spreader assembly 50 may have side surfaces 61 that are beveled away from the heat receiving surface of the heat spreader 56 at a fairly steep angle. In some embodiments, the side surfaces 61 may have a bevel angle (e.g., with respect to an upper surface of the adjacent heat spreader 56) that is within a range of 30° to 60°, inclusive.

The heat spreader assembly 50 may be constructed in a similar manner as the construction of the heater assembly 30, described above.

Figure 10:
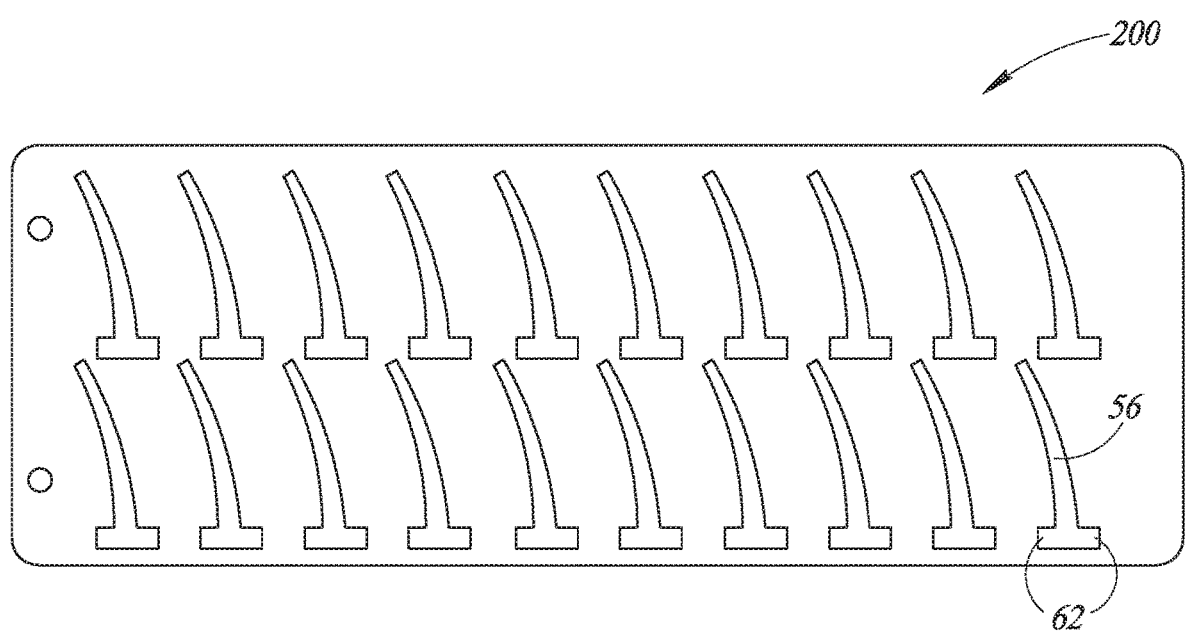
FIG. 10 is a top view illustrating a sheet of material from which a plurality of heat spreaders is formed, in accordance with one or more embodiments.

FIG. 10 illustrates a sheet 200 of thermally conductive material from which a plurality of heat spreaders 56 may be formed. The heat spreaders 56 may be etched or stamped out of the sheet 200. In some embodiments, the sheet 200 may be substantially the same as the multi-unit frame 100 shown and described with respect to FIG. 6. In some embodiments, the sheet 200 is a sheet of half hard beryllium copper (BeCu) having a thickness between about 0.005 inch and 0.02 inch, inclusive. In some embodiments, the sheet 200 is a sheet of half hard beryllium copper having a thickness of about 0.012 inch.

The tissue facing surface (e.g., the upper surface) of the heat spreader 56 may be coated with an anti-oxidizing and/or non-stick material, such as a ceramic layer of CrN. This coating prevents the heat spreader 56 from oxidizing and provides a non-stick layer on the surface of the heat spreader 56.

The tissue-facing surface of the heat spreader 56 may have a substantially same shape as the exposed ferromagnetic heater 36 of the heater assembly 30. For example, the heat spreader 56 may have a convex surface, and in some embodiments, the convex surface of the heat spreader 56 may have a slight rise along a center line of the surface, as shown in FIG. 8. In one or more embodiments, the rise along the center line of the heat spreader 56 may be within a range of about 0.001 inch to about 0.01 inch, inclusive, with respect to the lateral edges of the heat spreader 56. In some embodiments, the rise along the center line of the heat spreader 56 may be about 0.004 inch. The center line of the heat spreader 56 may be aligned with the center line of the ferromagnetic heater 36.

Figure 11:
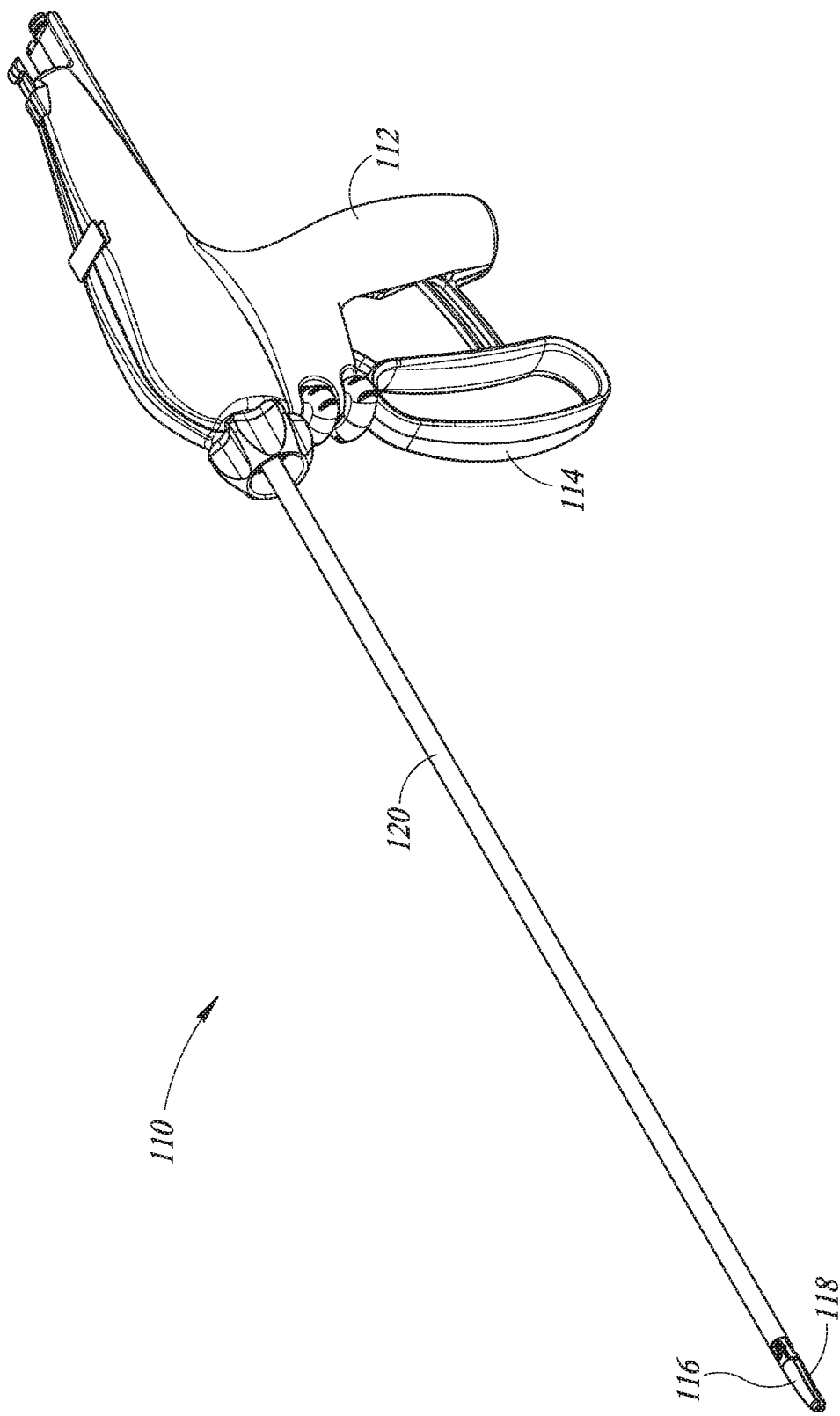
FIG. 11 is a perspective view illustrating a surgical device, in accordance with one or more embodiments.

FIG. 11 illustrates a handheld surgical device in the form of laparoscopic shears 110, in accordance with one or more embodiments of the present disclosure. The laparoscopic shears 110 includes a handpiece or body 112, a compression handle 114, and a shaft 120. First and second jaws 116, 118 are attached to the shaft 120, and the first and second jaws 116, 118 may be closed, for example, by pulling the compression handle 114 inward toward a handle portion of the body 112.

The first and second jaws 116, 118 of the laparoscopic shears 110 may be substantially the same or similar to, and may include any or all of the features and functionalities of, the first and second jaws 16, 18 of the open shears 10 described herein. In some embodiments, the first and second jaws 116, 118 of the laparoscopic shears 110 may be machined or metal injection molded stainless steel. The first and second jaws 116, 118 include cavities which may be substantially the same as the cavities 17, 19 described herein with respect to the open shears 10, and a heater assembly and heat spreader assembly may be inserted into the cavities of the first and second jaws 116, 118 in a same way as previously described herein with respect to the open shears 10. The heater assembly and heat spreader assembly of the laparoscopic shears 110 may be substantially the same as the heater assembly 30 and heat spreader assembly 50 described herein with respect to the open shears 10.

Embodiments provided herein include several features that provide technological improvements. For example, embodiments provided herein facilitate proper alignment of the tissue facing surfaces of the heater assembly 30 and the heat spreader assembly 50. Proper alignment of such tissue facing surfaces is desirable to achieve a good seal of tissue, and the tissue facing surfaces of the heater assembly 30 and the heat spreader assembly 50 should come together in a way so that the tissue thickness in compression is uniform. This ensures that the temperature profile in the tissue is uniform along the seal length. In some embodiments, the jaws of the surgical devices provided herein may be biased slightly toward the toe of the jaws, and the toes of the jaws may come together first when the jaws are brought toward one another. This allows for a slight flexure in the structure (e.g., in the encapsulant 38 and/or the encapsulant 48) which may bring the tissue facing surfaces to a substantially parallel orientation when compression is applied. The stiff yet somewhat compliant structure of the heater assembly 30 and the heat spreader assembly 50, provided in part by the encapsulant 38 of the heater assembly 30 and the encapsulant 58 of the heat spreader assembly 50, advantageously facilitate the flexure for proper orientation of the jaws with respect to the tissue positioned therebetween.

Moreover, embodiments provided herein facilitate application of proper compression forces on the tissue. This is desirable to get a good seal, which is achieved in part through the application of sufficient compression on the tissue. As described with respect to the open shears 10, the force applied by a user to flex the arm 14 may be utilized to control the compression force applied to tissue to achieve a good seal. The flex of the arm 14 has a low spring rate due to its flexibility. As described with respect to the laparoscopic shears 110, the compression handle 114 which may be coupled to a spring, may be utilized to control the compression force. The compression force applied to the tissue may be degraded to a certain extent by the flexibility of the heater assembly 30 and the heat spreader assembly 50 (which may be due to the flexibility of the encapsulants 38, 58), flex of the jaws, and/or flex in the tool structure (e.g., the structure of the open shears 10 and/or the laparoscopic shears 110). All of these features which may have some flexibility may contribute together like springs in series. A certain amount of flex may be desirable to allow for proper jaw alignment (e.g., between the heater assembly 30 and the heat spreader assembly 50). This is aided by embodiments of the present disclosure in which the heater assembly 30 and the heat spreader assembly 50, when assembled within the respective jaws, have a lengthwise stiffness with some flexibility, for example, at the heel and the toe of the structures (e.g., at the proximal and distal ends of the heater assembly 30 and the heat spreader assembly 50).

Embodiments of the present disclosure further facilitate aligned cutting of tissue along a center line and sealing of the tissue adjacent to the center line. This feature is provided, at least in part, by the particular shapes of the tissue facing surfaces of the heater assembly 30 and the heat spreader assembly 50, for example, when positioned within the cavities 17, 19 of the jaws 16, 18. The tissue facing surfaces allow for the ferromagnetic heater 36 and the heat spreader 56 to come together in an aligned position such that the tissue is compressed enough in the center to achieve allow the tissue to be cut while allowing the tissue to the sides to seal. Additionally, the beveled structure on the sides of the encapsulant 38, 58 facilitate sealing and cutting of tissue while avoiding holding onto the tissue.

Although embodiments of the present disclosure have been described herein in which the heater assembly and heat spreader assembly are overmolded with an encapsulant material and then inserted into respective cavities within the jaws, in other embodiments, the heater assembly and/or the heat spreader assembly may be overmolded by the encapsulant after the underlying structures of the heater assembly and/or the heat spreader assembly are positioned within the respective cavity. For example, the underlying structures of the heater assembly and/or the heat spreader assembly may be positioned within a cavity in a jaw, and the encapsulant material (such as silicone rubber) may be injected directly into the cavity in the jaw, thereby encapsulating the heater assembly and/or the heat spreader assembly and filling the cavity and adhering the assembly within the cavity.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Application No. 62/750,747, filed Oct. 25, 2018, are incorporated herein by reference, in their entirety. Aspects of the embodiments can be modified, if necessary to employ concepts of the various patents, applications and publications to provide yet further embodiments.

Moreover, the various features of the representative examples and the dependent claims may be combined in ways that are not specifically and explicitly enumerated in order to provide additional useful embodiments of the present teachings. It is also expressly noted that all value ranges or indications of groups of parameters disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A surgical device, comprising:
a ferromagnetic heater assembly, including:
an electrical conductor having a first leg, a second leg, and a vertical bend connecting the first and second legs, the vertical bend located at a distal tip of the electrical conductor, the first and second legs being spaced apart from one another along a vertical direction between the distal end and a proximal end of the electrical conductor, the first leg including a first outer surface and a first inner surface, the first inner surface opposite the first outer surface, the second leg including a second outer surface and a second inner surface, the second inner surface facing the first inner surface, and the second outer surface opposite the second inner surface such that the second outer surface faces away from the first leg;
a ferromagnetic heater on the first leg of the electrical conductor, the ferromagnetic heater including a heating element that generates heat in response to current flowing through the electrical conductor; and
an encapsulant at least partially surrounding the heating element of the ferromagnetic heater and at least a portion of both the second inner surface and the second outer surface of the second leg opposite the ferromagnetic heater, a surface of the ferromagnetic heater being at least partially exposed by the encapsulant, wherein the surface of the ferromagnetic heater is a tissue-contacting surface that faces in the vertical direction; and
a first spacer positioned between the first inner surface and the second inner surface of the electrical conductor along the vertical direction such that the first spacer imparts vertical stiffness to the first leg and the second leg and limits vertical movement of the first leg towards the second leg upon application of pressure to the tissue-contacting surface, wherein the first spacer is surrounded by the encapsulant.

2. The surgical device of claim 1 wherein the encapsulant comprises silicone rubber.

3. The surgical device of claim 1 wherein side surfaces of the encapsulant are beveled at an angle with respect to the tissue-contacting surface of the ferromagnetic heater.

4. The surgical device of claim 3 wherein the side surfaces of the encapsulant are beveled at an angle within a range of 30° to 60°, inclusive, with respect to the tissue-contacting surface of the ferromagnetic heater.

5. The surgical device of claim 1 wherein the first spacer comprises polyimide.

6. The surgical device of claim 1, further comprising a second spacer on the second leg, the second leg positioned between the first spacer and the second spacer.

7. The surgical device of claim 1 wherein the electrical conductor comprises beryllium copper, and the ferromagnetic heater comprises a layer of nickel-iron alloy at least partially surrounding the electrical conductor.

8. The surgical device of claim 1 wherein the tissue-contacting surface of the ferromagnetic heater has a convex shape.

9. The surgical device of claim 1 wherein the first spacer is positioned between the first and second leg such that the spacer is elongate along a first direction extending away from the vertical bend and parallel to the first leg and the second leg.

10. A surgical device, comprising:
a first jaw having a first cavity;
a second jaw having a second cavity, the second jaw rotatably coupled to the first jaw about a pivot point, such that rotation of the second jaw relative to the first jaw moves the second jaw toward and away from the first jaw with respect to a vertical direction;
a ferromagnetic heater assembly positioned in the first cavity of the first jaw, the ferromagnetic heater assembly including:
an electrical conductor having a first leg, a second leg, and a vertical bend extending between the first and second legs, the vertical bend located at a distal tip of the electrical conductor, the first and second legs being spaced apart from one another along the vertical direction between the distal end and a proximal end of the electrical conductor, the first leg including a first outer surface and a first inner surface, the first inner surface opposite the first outer surface, the second leg including a second outer surface and a second inner surface, the second inner surface facing the first inner surface, and the second outer surface opposite the second inner surface such that the second outer surface faces away from the first leg;
a ferromagnetic heater on the first leg of the electrical conductor, the ferromagnetic heater including a heating element that generates heat in response to current flowing through the electrical conductor; and
a first encapsulant at least partially surrounding the heating element of the ferromagnetic heater and at least a portion of both the second inner surface and the second outer surface the second leg opposite the ferromagnetic heater, a surface of the ferromagnetic heater being at least partially exposed by the first encapsulant;
a first spacer positioned between the first leg and the second leg along the vertical direction thereby limiting movement of the first leg towards the second leg upon application of pressure to the first outer surface; and a heat spreader assembly positioned in the second cavity of the second jaw, wherein the heat spreader assembly includes:
a heat spreader;
a temperature sensor thermally coupled to the heat spreader; and
a second encapsulant at least partially surrounding the heat spreader and the temperature sensor.

11. The surgical device of claim 10 wherein the first encapsulant comprises silicone rubber.

12. The surgical device of claim 10 wherein side surfaces of the first encapsulant are beveled at an angle within a range of 30° to 60°, inclusive, with respect to the exposed surface of the ferromagnetic heater.

13. The surgical device of claim 10, further comprising a second spacer on the second leg, the second leg positioned between the first spacer and the second spacer.

14. The surgical device of claim 10 wherein the temperature sensor comprises a thermocouple.

15. The surgical device of claim 10 wherein the first encapsulant assembly has a shape corresponding to an interior shape of the first cavity in the first jaw, and the second encapsulant has a shape corresponding to an interior shape of the second cavity in the second jaw.

16. The surgical device of claim 10 wherein side surfaces of the second encapsulant are beveled at an angle within a range of 30° to 60°, inclusive, with respect to a surface of the heat spreader.

17. The surgical device of claim 10 wherein the first jaw is attached to a body of the surgical device, and the second jaw is attached to an arm of the surgical device, the arm being movable toward the body by rotation of the arm about the pivot point.

18. The surgical device of claim 10, further comprising:
a body including a handle portion;
a compression handle coupled to the body; and
a shaft between the body and the first and second jaws,
wherein the compression handle is movable toward the handle portion of the body, and motion of the compression handle toward the handle portion of the body causes the second jaw to rotate about the pivot point toward the first jaw.

19. A surgical device, comprising:
a ferromagnetic heater assembly, including:
an electrical conductor having a first leg, a second leg, and a vertical bend extending between the first and second legs, the vertical bend located at a distal tip of the electrical conductor, the first and second legs being spaced apart from one another along a vertical direction between the distal end and a proximal end of the electrical conductor, the first leg including a tissue contacting surface that faces in the vertical direction, and the second leg positioned opposite the tissue contacting surface;
a ferromagnetic heater on the first leg of the electrical conductor; and
an encapsulant at least partially surrounding the ferromagnetic heater, the bend of the electrical conductor, and a portion of the second leg opposite the ferromagnetic heater, a surface of the ferromagnetic heater being at least partially exposed by the encapsulant; and
a first spacer positioned between the first and the second legs of the electrical conductor with respect to the vertical direction so as to provide stiffness and maintain spacing along the vertical direction between the first leg and the second leg when the tissue contacting surface contacts tissue.

* * * * *